United States Patent [19]

Houghton et al.

[11] Patent Number: 4,936,140

[45] Date of Patent: Jun. 26, 1990

[54] DEVICE AND METHOD FOR CALIBRATING A NON-DESTRUCTIVE SHEET STRENGTH MEASURING SYSTEM

[75] Inventors: Paul J. Houghton, Los Gatos; John D. Goss, San Jose; Mathew G. Boissevain, Los Altos Hills, all of Calif.

[73] Assignee: Measurex Corporation, Cupertino, Calif.

[21] Appl. No.: 146,930

[22] Filed: Jan. 22, 1988

[51] Int. Cl.$^5$ .............................................. G01L 5/04
[52] U.S. Cl. ..................................................... 73/159
[58] Field of Search ................. 73/1 R, 1 B, 159, 838, 73/862.54, 862.55; 162/263, 49

[56] References Cited

U.S. PATENT DOCUMENTS 2,522,544  9/1950  Seyboth .................................. 73/159
3,498,120  3/1970  MacMillan ............................. 73/838
3,552,203  1/1971  Freeh .................................... 162/263
3,738,151  6/1973  Giunta et al. .......................... 73/1 B

FOREIGN PATENT DOCUMENTS 0110663  4/1928  Fed. Rep. of Germany ......... 73/159
0248888  3/1926  United Kingdom ................... 73/159
0934328  8/1963  United Kingdom ................... 73/159
1121147  7/1968  United Kingdom ................... 73/159

Primary Examiner—Robert Raevis
Attorney, Agent, or Firm—Spensley, Horn, Jubas & Lubitz

[57] ABSTRACT

A running blade is adapted to move at the same speed as a continuously running sheet and to generate a burst perforation through the sheet. The force exerted by the blade against the sheet is measured and used to calibrate a non-destructive sheet strength sensor.

32 Claims, 5 Drawing Sheets

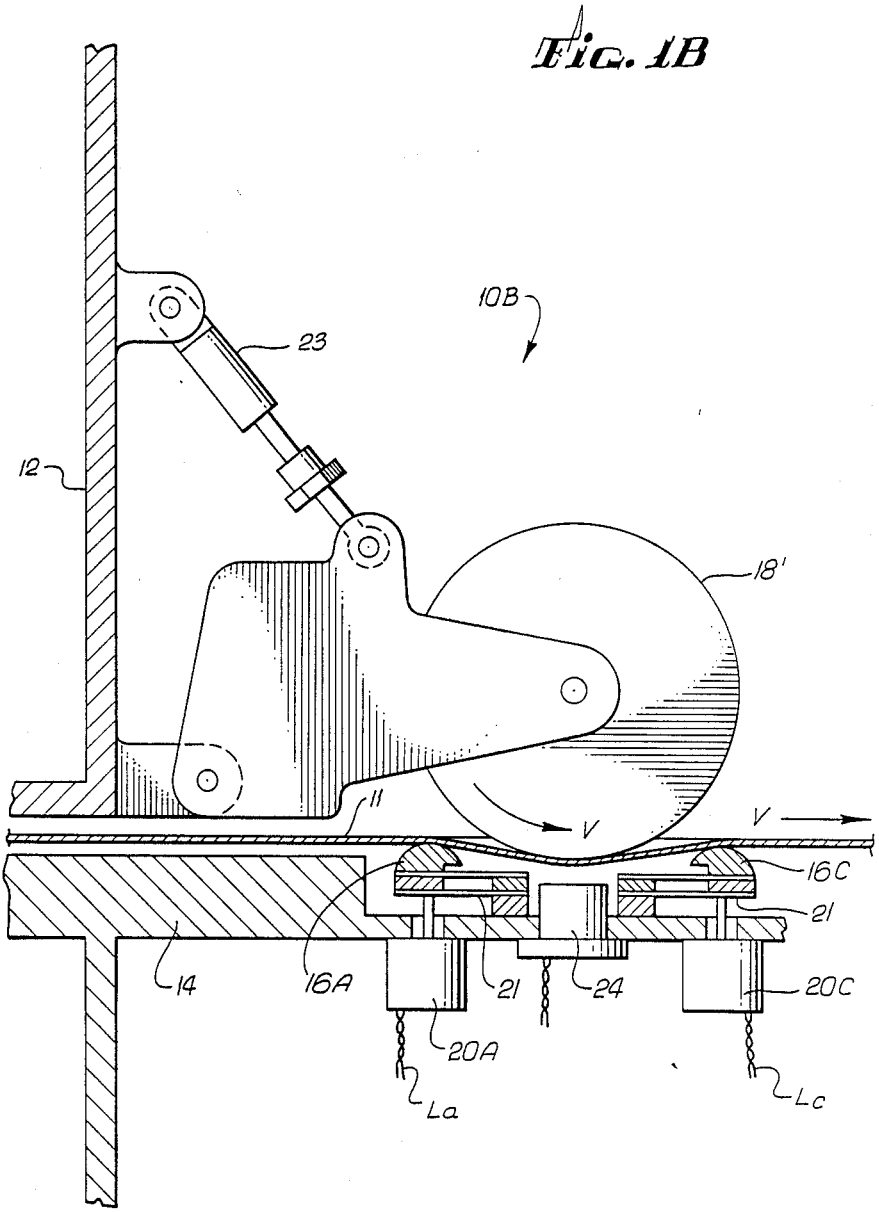

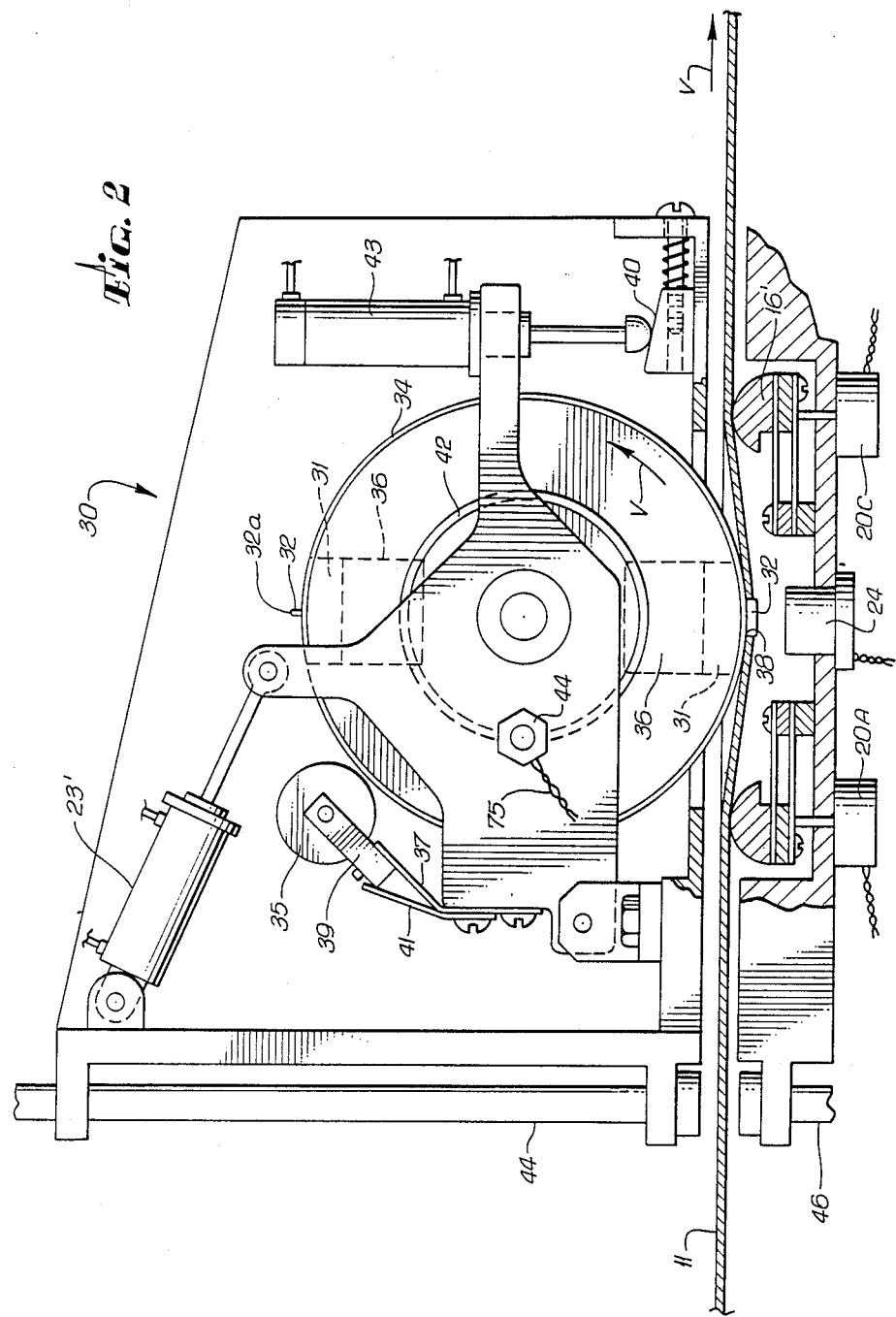

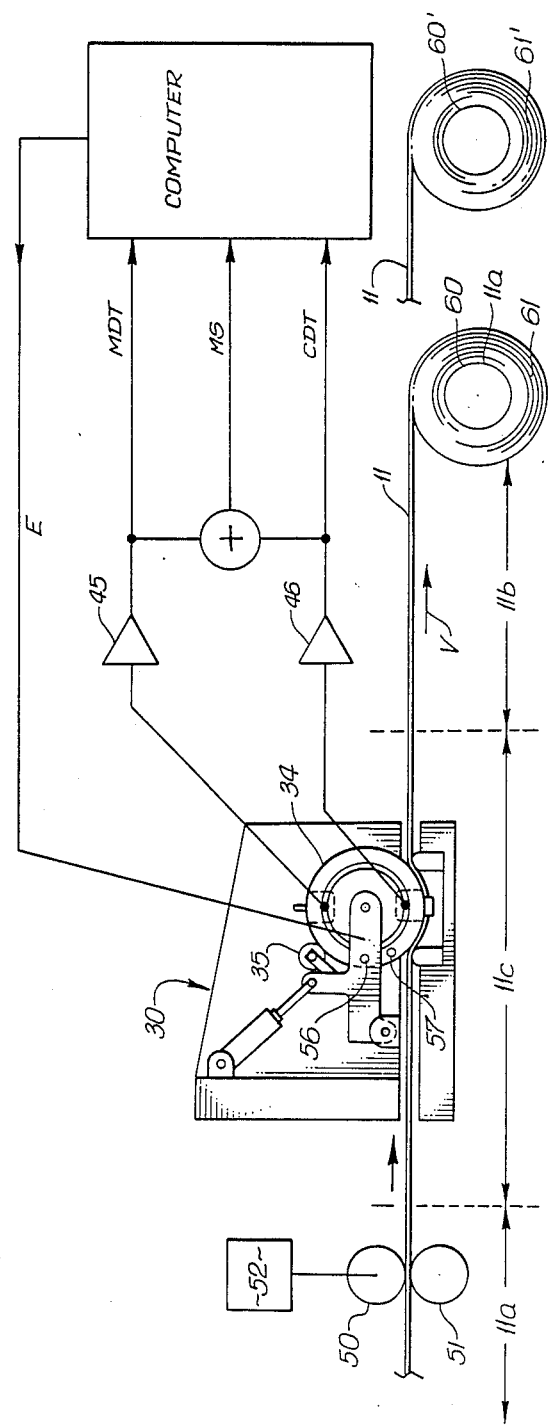

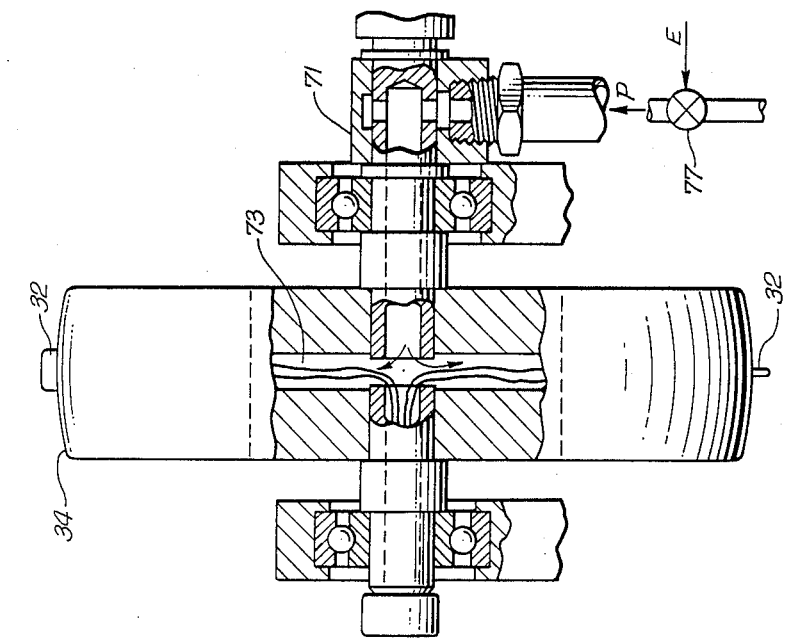
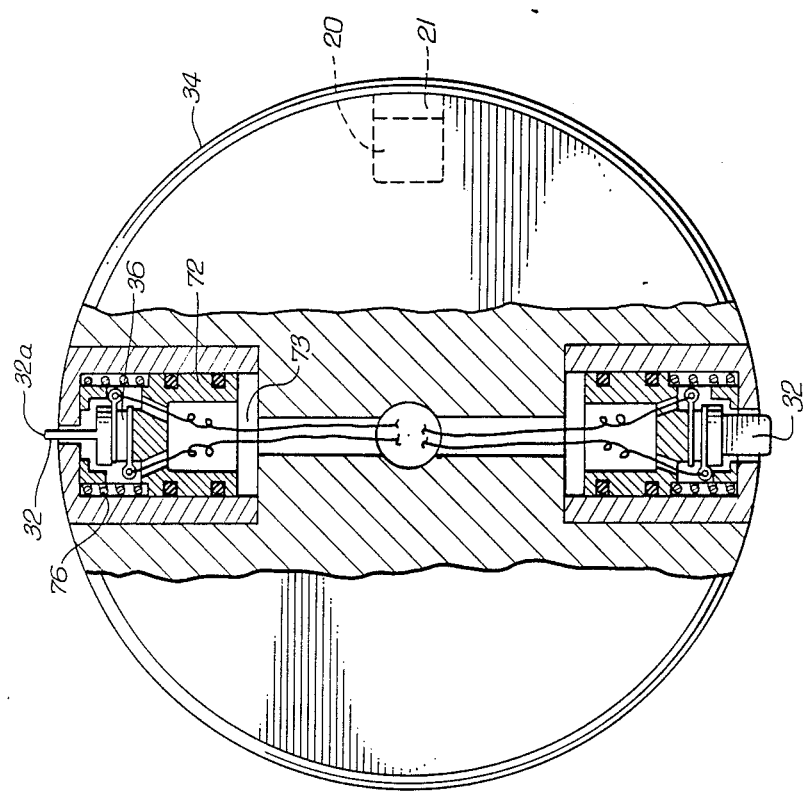

DEVICE AND METHOD FOR CALIBRATING A NON-DESTRUCTIVE SHEET STRENGTH MEASURING SYSTEM

BACKGROUND OF THE INVENTION

The present invention is directed to continuous sheet processing such as is found in the papermaking industry, and more particularly to a device and method for calibrating a non-destructive sheet strength measuring system adapted for such continuous processing.

Non-destructive methods and devices for determining the strength of a continuously moving sheet are disclosed in commonly-owned U.S. applications Ser. No. 730,406, filed May 2, 1985 and Ser. No. 920,107, filed Oct. 16, 1986, and in U.S. Pat. No. 4,864,851, issued Sept. 12, 1989 and U.S. Pat. No. 4,866,984, issued Sept. 19, 1989. These applications and patents are incorporated herein by reference. Using the methods and devices disclosed in these applications and patents, the burst strength of a sheet can be computed without damaging the sheet. The term "burst strength" is used herein to denote both a uniformly directed (omni-directional) burst such as occurs, for example, in the well known Mullen test for determining paper strength and a uni-directed burst such as would occur in a tensile test wherein a sheet sample is pulled apart in a specific direction relative to its length.

The methods disclosed in the cited applications and patents, and the devices for performing these methods, rely upon the relationship between the burst strength of a sheet (e.g. a paper sheet) and the force required to deflect the sheet into an unsupported region. In brief, the methods disclosed in these applications comprise the steps of: supporting the moving sheet around an unsupported region (e.g. with an annular support); non-destructively deflecting the sheet into the unsupported region; measuring the amount of force exerted to cause the deflection; and calculating the burst strength of the moving sheet from the measured deflection force using empirically determined mathmatical formulas which relate deflection force to sheet burst strength.

Preferably, the moving sheet is deflected by a constant distance into the unsupported region and is moved by rollers which span the width of the sheet and hold the sheet under a constant tensile force. However, if the tensile force on the moving sheet and the amount of deflection cannot be held constant, then the value of the sheet strength which is calculated based upon the deflection force may be further refined by incorporating into the strength calculation one or more variables indicative of the changing tensile force and the changing distance that the sheet is deflected into the unsupported region. Values indicative of the sheet velocity, basis weight and thickness may also be utilized in the strength calculations. Sheet strength equations which incorporate values indicative of these parameters are disclosed in the previously cited applications.

FIG. 1A is a cross-sectional view of one portion of a non-destructive strength measuring system 10A which is disclosed in U.S. Pat. No. 4,864,851. In this system, the upper and lower sensor supports, 12 and 14, are provided over-lapping opposed sides of a moving sheet 11. The annular sheet support (or "ring") 16 is disposed on the lower sensor support 14 with an upper surface 16a of the ring 16 contacting the moving sheet 11 to support the sheet in an annular fashion. A rotatable sensor wheel 18 is aligned with the hole in the center of the ring 16. The sensor wheel 18 is brought into contact with the upper surface of the sheet 11 to deflect the unsupported portion of the moving sheet 11 below the top surface 16a of the ring 16. The wheel 18 is rotated by frictional contact with the moving sheet 11 so that the wheel 18 moves at the same velocity as the sheet 11 and thus does not to abrade the top surface of the sheet 11. A piezoelectric force sensor 20 and a radially displaceable button 21 are provided at the periphery of the wheel 18 for determining the amount of force exerted between the sheet 11 and sensor wheel 18 when the sheet 11 is deflected into the center of the ring 16. A slip ring coupler 22 connects the sensor 20 to an electronic computer to supply the computer with force measurement signals, F, from the piezoelectric force sensor 20.

An air actuated piston 23 determines the distance that the wheel 18 deflects the sheet 11 below the upper ring surface 16a. For added accuracy, a distance measuring sensor 24, which may, for example, be a magnetic reluctance gap detector, may be provided on the lower support 14 to precisely measure the amount of deflection. The deflection distance is sent to the computer as a vertical deflection distance signal Z. The signals, F and Z, from sensors 20 and 24, respectively, are received by the computer and used to calculate the sheet burst strength using the empirically determined formulas disclosed in the cross-referenced applications and patents.

The empirical formulas include certain fixed values that are set prior to a strength measurement run and other run-time variable parameters, including values representing the measured amount of deflection and deflection force. For example, U.S. Pat. No. 4,864,851 discloses the following paper sheet strength equation for use with the strength measuring system 10A when it is positioned downstream of the calender stack in a papermaking machine:

$$S = A \times f(Z) \times \frac{L}{L_{AV}} + (B \times W^E \times T^F) - C \times V^D \quad (1)$$

where

S is the computed sheet strength which correlates with the Mullen strength,

L is the instantaneous deflection force as measured by the piezoelectric force sensor 20, $L_{AV}$ is the average deflection force across the width of the sheet 11 as measured by the piezoelectric force sensor 20, W is the basis weight of the sheet 11, T is the thickness of the sheet 11, V is the velocity of the paper leaving the last calender roll of the paper making machine, f(Z) is a function of the deflection distance, Z, and A,B,C,D,E and F are constants.

The values of the constants may be experimentally determined using well known equation curve fitting techniques. Similarly, the function f(Z) can also be experimentally determined by taking deflection force measurements of a sheet having known constant basis weight, thickness, velocity and strength, and solving the equation (1) for f(Z).

FIG. 1B shows a cross sectional view of another continuous-run non-destructive strength measuring system 10B which is disclosed in the above-referenced U.S. Pat No. 4,866,984. Like elements are referenced by numbers corresponding to those of FIG. 1A and need not be described again. This strength measuring system operates in a manner similar to the system of FIG. 1A. However, the support ring of this particular embodiment is quadrally divided into segments 16A, 16B, 16C and 16D (only two shown) with each segment being suspended by a spring 21 having a predetermined suspension force. A corresponding set of force measuring sensors 20A–20D (two shown) are coupled to the respective ring segments 16A–16D for developing respective deflection force signals $L_a$, $L_b$, $L_c$, and $L_d$ (only two illustrated) of which, one pair, $L_a$ and $L_c$, indicate machine direction force parameters and a second pair, $L_b$ and $L_d$, indicate cross-direction force parameters. The $L_a$ and $L_c$ force signals are generated by the force sensors 20A and 20C associated with the ring segments disposed on opposite sides of the ring in the machine direction, as illustrated in FIG. 1B. The remaining two force signals, $L_b$ and $L_d$, are generated by the force sensors 20B and 20D associated with the remaining two opposing ring segments. It is to be noted that the slip ring coupler 22 and wheel mounted sensor 20 of FIG. 1A are not required for the sensor wheel 18' of FIG. 1B.

Using the strength sensor system of FIG. 1B, the sheet strength can be non-destructively determined in both the machine direction and the cross direction. For example, U.S. patent application Ser. No. 920,107 discloses the following sheet strength equations for calculating sheet strength in the machine direction and the cross direction:

$$S_{md} = A \left[ \frac{L_a + L_c}{(C + Z)(T_n + F)} \right]^H + E \quad (2)$$

and $$S_{cd} = B \left[ \frac{L_b + L_d}{(D + Z)(T_n + G)} \right]^J + E \quad (3)$$

where $S_{md}$ and $S_{cd}$ are, respectively, the machine and cross direction sheet strengths. $T_n$ is the average sheet tension measured across the entire width of the sheet, Z is the amount of sheet deflection and A,B,C,D, E,F,G,H, and J are constants. As in equation (1) above, the constants are empirically determined using well known equation curve fitting techniques. Z may be determined using the previously mentioned magnetic reluctance gap detector. Techniques and devices for measuring sheet tension are also known. The constant E need not necessarily have the same value in both equations (2) and (3).

U.S. patent application Ser. No. 920,107 also discloses that the Mullen strength may be computed with the following equation which combines the outputs from all four of the split ring force sensors:

$$S_{mu} = A \left[ \frac{L_a + L_c}{(C + Z)(T_n + F)} \right]^H + B \left[ \frac{L_b + L_d}{(D + Z)(T_n + G)} \right]^J + E \quad (4)$$

where $S_{mu}$ is the Mullen strength and the other parameters are the same as previously disclosed. The constants, however, are not necessarily the same values in each of equations 1–4.

The non-destructive sheet strength measuring sensors of FIGS. 1A and 1B may be scanned back and forth across the width of sheet as the sheet is being continuously produced by the sheet forming machine. The signals from these sheet strength sensors may then be sent to a computer which determines the strength profile of the sheet in both the machine and cross directions. The strength profile can then be displayed to the operator either in graphical form or numerically. Based upon the displayed profile, the operator may adjust the operation of the sheet forming machine to increase or decrease the overall sheet strength or to adjust the sheet strength in one or more localized areas across the width of the sheet. For example, in a paper mill, the mill operator can adjust the sheet strength by increasing or decreasing the degree to which the pulp is refined, by changing the jet-to-wire ratio or by altering the volume of the flow of pulp from the headbox at one or more particular areas across the width of the sheet. Other means for adjusting the overall strength of paper sheet and the sheet strength at localized areas are known in the art.

While the non-destructive strength measuring systems 10A and 10B of FIGS. 1A and 1B overcome many problems associated with previously known destructive methods for determining the burst strength of a sheet 11, there still remained a problem of how to calibrate such systems relative to industry accepted standards based upon destructive strength testing. To complicate matters further, in some circumstances it may be necessary to calibrate the systems relatively frequently. For example, in papermaking, the relationship between the burst strength of the paper sheet and the force required to deflect the sheet can change as a result of using different types of trees for the raw material, as a result of wood fiber length changes, changes in lignin content of the wood and so forth.

Prior to the present invention, sheet samples had to be periodically obtained from the continuous sheet production line and the results of destructive laboratory strength tests of these samples used to calibrate the non-destructive sheet strength measuring systems. The samples were cut from a sheet and sent to the laboratory for destructive testing. The samples were then placed in a standard stationary testing instrument where, for example, the burst strength of the paper sheet was determined by industry accepted methods such as the destructive Mullen burst pressure test and/or tensile strength testing in the machine direction and cross direction. The non-destructive strength measuring system (e.g. 10A or 10B) was then calibrated with the strength values obtained from these industry accepted stationary standard destructive tests. Such calibrations were performed by altering the values of the constants in the strength equations so that the strength values obtained from the non-destructive strength measuring systems agreed with the laboratory strength measurements.

The non-destructive sheet strength measuring systems of the previously referenced co-pending applications represent a great advance over the prior art since they permit continuous monitoring of the sheet strength, without damage to most of the sheet. Nevertheless, the process of periodically obtaining samples from the production line and bringing the samples to the laboratory for destructive testing to calibrate the non-destructive strength measuring systems can be a source of undesirable delay. Specifically, relatively long periods of time may pass while the laboratory tests are performed before it is discovered that the non-destructive sheet strength measuring system is out of calibration. In the corresponding interim, a large amount of sheet material can be produced. However, the strength of such sheet material will be questionable because of the non-calibrated condition of the non-destructive strength measuring system. Thus, there is a need for the present calibration system which can periodically calibrate the strength measuring systems of the referenced applications automatically and with minimal delay.

SUMMARY OF THE INVENTION

It is an object of the present invention to provide a method and device for quickly and automatically calibrating a non-destructive sheet strength measuring system.

The applicants have determined that the burst strength values of a sheet material, such as paper, can be directly related to the amount of force required to generate perforations in the sheet. In accordance with the present invention, small puncture holes or perforations are made at the beginning and/or end portions of a moving sheet which may be on a sheet production line and which is to be rolled onto a collection reel. The force required to puncture the sheet is measured and used to determine the sheet strength. The puncture-force derived sheet strength value is then used to calibrate the previously described non-destructive sheet strength measuring systems. Since the beginning and end portions of such a rolled sheet are normally either discarded or used for laboratory tests, and since the puncture holes can be made in the sheet while the sheet is moving along the production line, the puncturing process does not interfere with the efficiency of the sheet manufacturing process.

In one embodiment of the present invention, projecting "blades" having blunt edge portions are disposed at the periphery of a rotatable calibration wheel. The blades are automatically brought into contact with the moving sheet and their blunt edge portions are forced through the sheet repeatedly as the wheel rotates. Puncture force sensors are provided for measuring the amount of force exerted by the blades to puncture the sheet. Preferably, at least two blades are provided on the wheel with blunted edges that are elongated orthagonally to one another while being respectively aligned lengthwise in the machine direction and cross direction of the continuously moving sheet. Force signals obtained from the puncture force sensors associated with the machine direction oriented blade are used to determine the cross direction tensile strength of the sheet, the puncture force signals from the cross direction oriented blade are used to determine the machine direction tensile strength of the sheet and a weighted average of signals from the force sensors associated with both blades may be used to determine a nondirectional sheet strength value, such as the well known Mullen strength.

To use the calibration wheel of the present invention, the wheel is first run over a variety of sheets made of the material desired to be tested (e.g. paper) so that the blades puncture the sheets and the puncture force measurements are obtained. Each of these sheets has a different known strength. In this way, a graph or chart of puncture force values can be created to relate the different puncture forces directly to the known sheet strength values. The greater the sheet strengths, the greater the puncture force. Thereafter, no additional laboratory tests will be necessary to determine sheet strength since each measured puncture force will be known to correspond to a particular Mullen, tensile or other destructive laboratory strength measurement.

As previously mentioned, the projecting blades should have blunt edges. Blunt edged blades are preferred because sharp edged blades will tend to dull or blunt with use. As these sharp edged blades become dull, increasing force will be required to puncture the sheet. Thus, the correspondence between the puncture force and sheet strength will change continually with the wear of these blades. This wearing out effect of sharp blades adds an undesirable complication to the calculation of the sheet strength. Therefore, blunt edged blades are preferred. Moreover, although blunt edged blades are preferred to avoid the problem associated with the wearing out of sharp blades, the blades should nevertheless not be so blunt that the puncture holes produced by the elongated blades are no longer approximately the same shape as the blades. It is important that the puncture holes produced by the elongated blades have approximately the same shape as the blades to maintain the directional strength sensitivity of the orthogonally oriented blades.

Puncture force measurements may be made at the beginning and/or the end of a sheet production run. The measured puncture forces can then be related to known sheet strengths using the graph or chart constructed previously. Preferably, the chart of puncture forces and sheet strength values is stored in the computer which runs the non-destructive sheet strength measuring system. Signals from the puncture force sensors can then be transmitted to the computer which determines the sheet strength using the stored chart of values. Then, the computer compares the sheet strength values obtained from the stored chart with the sheet strength values obtained from the non-destructive sheet strength measuring system. If the non-destructive sheet strength calculations do not agree with the puncture-derived strength values, the values of the constants in the strength equations are adjusted to arrive at the correctly calibrated sheet strength values.

The above-described calibration process has many advantages. For example, the calibration process may be performed periodically, quickly and automatically under computer control, without the need for operator intervention or delay. Also, the calibration process may be performed without the need to cut out samples of the sheet. Moreover, once the initial table of values relating puncture forces to laboratory strength measurements is created, additional time consuming and expensive laboratory tests are unnecessary.

Once the non-destructive strength sensors are calibrated, the computer developes a graphical or numerical display of the correctly calibrated sheet strength profile. As previously mentioned, the operator can alter the operating characteristics of the sheet forming machine in response to the displayed profile to obtain the desired sheet strength. Alternatively, however, with the present invention, the computer which calculates the sheet strength can also be the process control computer for the sheet manufacturing facility. Based upon the calculated sheet strength profile, the process control computer can be programmed to automatically (or with operator assistance) adjust the operating characteristics of the sheet forming machine to obtain the desired sheet strength values. For example, in a paper mill, the process control computer could adjust the degree of pulp refining, the jet-to-wire ratio, the flow of the pulp from the headbox, etc., based upon the calculated sheet strength values.

BRIEF DESCRIPTION OF THE DRAWINGS

FIGS. 1A and 1B are cross-sectional side views of the non-destructive strength measuring systems disclosed in previously filed commonly assigned U.S. patents.

FIG. 2 is a cross-sectional side view of a sheet puncturing apparatus constructed in accordance with the present invention.

FIG. 3 is a perspective view showing the top and side of a puncturing calibration device which may be used in accordance with the present invention to calibrate the strength measuring systems of FIGS. 1A and 1B, and which may be scanned back and forth across the width of the sheet.

FIG. 4 is a block diagram showing how the puncturing apparatus of FIG. 2 can be incorporated in a continuous-run sheet production facility.

FIGS. 5 and 6 are, respectively, a cross-sectional side view and a partially sectioned front view of a puncturing calibration wheel which can be integrally formed in a multifunction fashion with a non-destructive strength measuring system such as shown in FIGS. 1A and 1B.

DETAILED DESCRIPTION OF THE PREFERRED EMBODIMENT

Figure 1A:
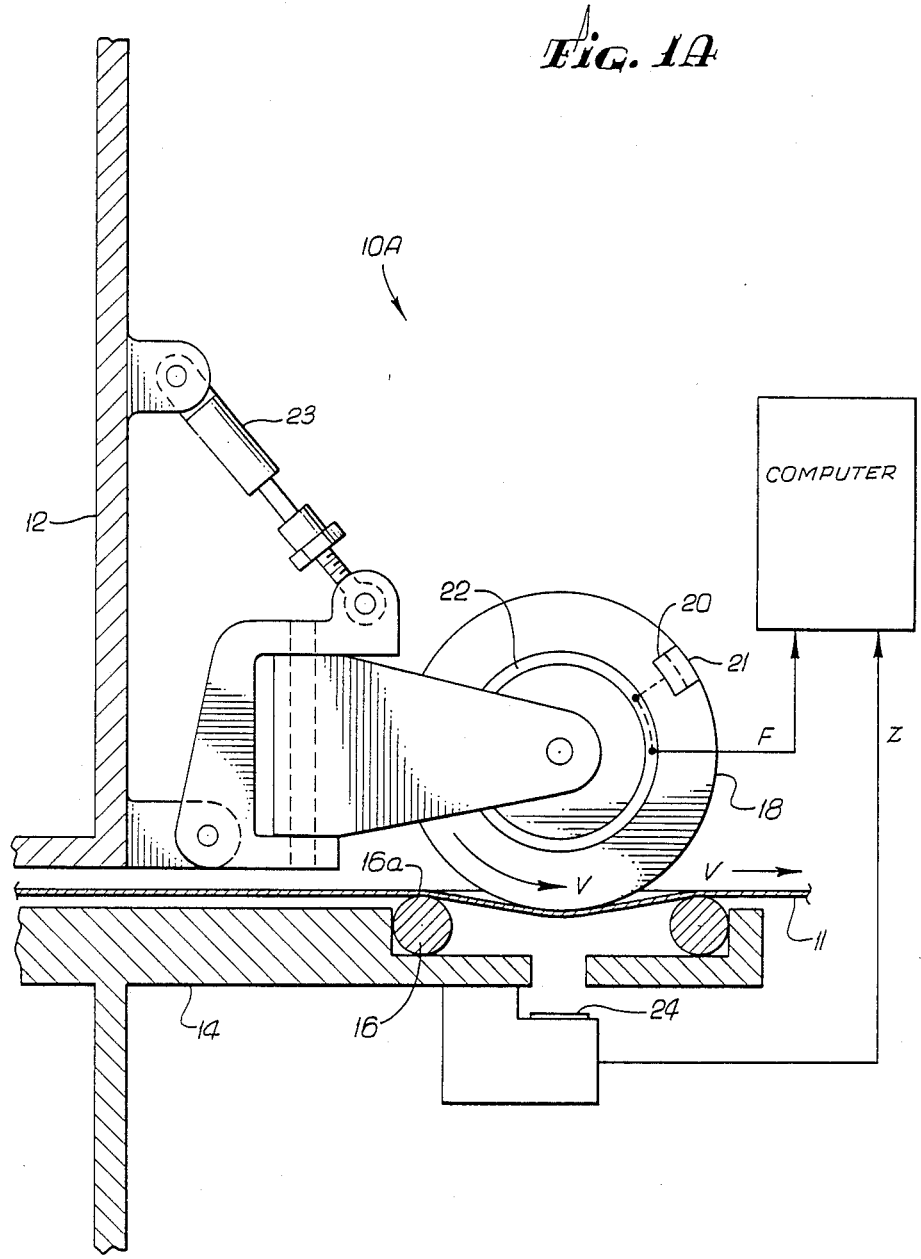

FIG. 2 is a cross-sectional view and FIG. 3 is a perspective view of a puncturing device 30 constructed in accordance with the present invention. One or more paper puncturing blades 32 having blunt ends 32a are provided projecting from the periphery of a rotatable wheel 34. The blades are mounted on radially displaceable buttons 31 provided within the calibration wheel 34. Puncture force sensors 36 are further provided within the puncture wheel 34 for generating electrical signals indicative of the amount of force exerted by the blades 32 when these blades create perforations 38 in the moving sheet 11.

A mercury slip ring coupling device 42/44 is used to provide an electrical connection between the rotating sensors 36 and a computer which receives and processes the force signals from the sensors 36.

A quadrally split backing ring 16', like that of FIG. 1B, is provided at the underside of the continuously moving sheet 11 to annularly support the sheet 11. The puncture wheel 34 is aligned with the sheet region supported annularly by the backing ring 16' and brought to bear against the top surface of the sheet 11 so that the blades 32 will create a series of puncture holes 38 in the sheet 11. Preferably, the periphery of the wheel 34 should be rotating at the same velocity V as the sheet 11 so that, except for the intended punctures 38, the wheel 34 will not tear the sheet 11. As described in greater detail below, the blades 32 may be retracted into the wheel 34 to allow the device to function in the previously described non-destructive sheet strength measuring mode.

The wheel 34 and backing ring 16' are respectively supported by upper and lower sensor supports, 44 and 46, which may also be used to move the wheel 34 and backing ring 16' in a scanning motion transversely across the width of the paper sheet 11 (i.e., in the cross direction, as shown in FIG. 3) to test transversely displaced portions of the sheet. Puncturing through the edge of the sheet 11 should generally be avoided so as not to initiate a tear across the entire width of the sheet 11.

A reference wheel 35 having a periphery made of a material with a known hardness, such as nylon, urethane or other hard plastic, is rotatably mounted to a mounting block 39 at the end of a 45° inclined leaf spring 37 of a known stiffness. The reference wheel 35 is periodically impacted by the blades 32 as the wheel 34 rotates to provide force calibration signals from the force sensors 36. A second leaf spring 41 is mounted to frictionally rub against the mounting block 39 and to thereby absorb residual vibrations of the inclined leaf spring 37 after the reference wheel 35 is struck by each of the blades 32. Since the force of the blades against the reference wheel 35 will be known, the reference wheel 35 may be used to calibrate the signals from the puncture force sensors 36.

A first air piston 23' brings the wheel 34 into engagement with the sheet 11. A second air piston 43 can be used to stop the wheel 34 at a preset position, as established by a screw-adjusted wedge 40. A first distance measurement is taken by a vertical distance measuring sensor 24 when the second piston 43 is retracted to cause the puncture wheel 34 to contact the vertical distance sensor 24 (there is no sheet material 11 in the system at this time). A second distance measurement is taken with the second piston 43 extended. The measurements taken at the two positions are then used to calibrate the readings of the vertical distance measuring sensor 24.

FIG. 4 is a block diagram showing how a puncturing device in accordance with the present invention can be incorporated into a sheet production line. Like reference numerals are used to denote like elements previously described. A sheet supply means such as calendering rollers 50, 51 feed an elongated sheet 11 of a burstible material (e.g. paper) to a collecting reel 60 at a predetermined velocity V. A constant force between the supply means 50, 51 and the collection reel 60 keeps the sheet substantially flat. When the collecting reel 60 has accumulated a predetermined length of the sheet, the sheet 11 is cut to thereby form the end of a first roll 61 and the beginning of a subsequent roll 61'. The subsequent roll 61' is taken up on a new collecting reel 60', which also, preferably, holds the sheet under the same known constant force.

The initial length of the sheet, first taken up by a fresh collecting reel 60, constitutes a begin-run (or take-up) section 11a which is normally discarded when the sheet is re-rolled or otherwise further processed after being accumulated onto the collection reel 60. The opposed terminal end of the rolled sheet constitutes an end-run (or turn-up) section 11c which likewise is normally discarded prior to the completion of manufacture. The discarded portions, 11a and 11c, can therefore be punctured with the blades 32 of the wheel 34 without damaging valuable sheet material. The midsection 11b of the sheet is much longer than either of the begin-run 11a or end-run 11c sections and constitutes a bulk portion of the sheet 11. If the bulk portion of the sheet is left intact, perforating either of the terminal sections, 11a and 11c, of the sheet will not affect the efficiency of the sheet manufacturing process.

FIG. 5 is a partial sectional detail side view of the calibration puncture wheel 34 and FIG. 6 is a partially opened detail view of the front of that wheel 34. As illustrated in these figures, the burst perforating blades 32 are retractably disposed in a multi-function wheel 34 which is adapted to also serve as the non-destructive sheet deflecting wheel of, for example, the systems of FIGS. 1A and 1B. Each blade 32 is attached to a piezoelectric force sensing crystal 36 and mounted to a retractable piston platform 72. A blade retracting spring 76 urges each perforating blade 32 to remain fully retracted within the multi-function wheel 34 while the midsection 11b of a running sheet is passing through the strength sensor. In this case, the multi-function wheel 34 is functioning in substantially the same manner as the nondestructive sensor wheels 18 or 18' of FIGS. 1A and 1B.

As shown in FIG. 4, a section detecting means 52 measures the length of sheet fed through rolls 50, 51 and signals the computer when the terminal sections 11a, 11c are passing under the wheel 34. The computer then transmits an engage command, E, causing the blades 32 of the wheel 34 to extend past the periphery of the wheel 34 and engage the sheet 11. The blades 32 then begin to produce a series of burst perforations 38 in the sheet 11 while the piezoelectric puncture force sensors 36 transmit pulsed signals to the computer indicating the amount of force exerted by each of the blades 32 against the sheet 11 as the blades 32 puncture the sheet 11.

When the computer issues the engage signal, E, a valve 77 (FIG. 6) opens to allowed pressurized air, P, into piston chambers 73 of the multi-function wheel through a rotary pressure coupler 71. The pressurized air, P, forces the blades 32 radially outwardly against the force of the springs 76 so that the blades 32 project beyond the periphery of the multi-function wheel 34.

Preferably, the blades 32 are provided with elongated blunt edges alternately oriented in the cross direction and in the machine direction. Signals from the puncture force sensors 36 associated with these alternately oriented blades 32 are transmitted serially through a conductive rotary coupling 42/44, amplified by amplifiers 45, 46 (FIG. 4), and time-wise demultiplexed to produce respective MDT and CDT signals, respectively indicative of the machine direction tensile strength and cross direction tensile strength of the sheet 11. For increased accuracy, a number of MDT and CDT signals should be averaged. The MDT signal is produced by the sensor 36 associated with the blade 32 having an edge 32a elongated in the cross direction while CDT signals are produced by the sensor 36 associated with the blade elongated in the machine direction. The MDT and CDT signals may be combined to produce a composite signal, MS, representitive of the Mullen strength of the sheet. The MS signal is a weighted average of the CDT and MDT signals. The weighting of these two signals necessary to achieve an MS signal indicative of the Mullen strength is dependent upon the dimensions of the various device components and, therefore, for any particular device, must be determined experimentally. Generally, however, with paper sheet material the MS signal will be weighted heavily toward the CDT signal. Accordingly, signals are developed for empirically calculating the Mullen strength, the machine direction tensile strength and the cross direction tensile strength of the sheet, and for calibrating the nondestructive strength sensors.

A wheel angle sensor 56 (FIG. 4) detects the angular state of the puncture wheel 34 and thereby identifies which of the serially transmitted signals produced from the force sensors 36 belongs to which of the blades 32, and whether they arise from contact with the reference wheel 35 or the sheet 11. The wheel angle sensor 56 may be, for example, a Hall effect device that detects an index hole 57 in the side of the puncture wheel.

With regard to the dimensions of the calibration puncture wheel 34, it has been found that a wheel 34 having a peripheral diameter of 5 inches and a width of 1.25 inch was well suited for use with paper sheets. The periphery of the wheel 34 was rounded to be, in effect, a spherical surface segment of a hypothetical sphere having a 5 inch diameter. The blades 32 were selected to project approximately 0.1 to 0.3 inch beyond the periphery of the wheel 34. The blades 32 were approximately 0.10 to 0.125 inches long by 0.020 to 0.062 inches thick. The puncturing edges of the elongated blades 32a were blunted to have an edge radius of 0.031 inch. The ends of the elongated blades were rounded to a radius of 0.020 to 0.062. The sheet velocity was nominally set to approximately 2000 feet per minute. The backing ring 16' was chosen to be of approximately the same inside diameter as the peripheral diameter of the puncture wheel 34.

Some of the advantages of the multi-function wheel, namely the avoidance of using both a single-function non-destructive deflecting wheel and a second single-function puncturing calibration wheel, along with their corresponding signal coupling devices, will be apparent from the above discussion. Another advantage of the multi-function wheel 34 may not be readily apparent. Since the multi-function wheel is already rotating at the velocity V of the running sheet 11 while the wheel 34 is in its non-destructive sensing mode, when an end-run section, for example, 11c of FIG. 4 approaches, there is no need to change the rotational velocity of the multi-function wheel 34 as the retractable blades 32 are projected outwardly to begin the perforation mode. The danger of a speed mismatch between the puncture blades 32 and the sheet 11, which would rip the sheet 11, is therefore obviated and only a relatively small part of the end-run and/or begin-run sections are therefore needed for destructive calibration.

In operation, the blades 32 are retracted and the wheel 34 is slowly engaged with the moving sheet until the wheel 34 deflects the sheet 11 inside the ring 16' by a desired amount and the friction between the wheel 34 and the moving sheet 11 causes the periphery of the wheel 34 to move at the same velocity as the sheet 11. Signals from the deflection force sensors 20A, 20B, 20C and 20D (only two shown) are sent to the computer, which uses one or more of the previously discussed strength equations to non-destructively and continuously determine the sheet strength. When a begin-run 11a or end-run 11c sheet section passes under the wheel 34, the blades 32 are extended and puncture force signals are transmitted to the computer. As previously mentioned, the computer contains a chart of puncture force values, each of which is associated with a particular sheet strength value. As also previously mentioned, if necessary, the computer then alters the value of the constants in the sheet strength equations so that the sheet strength values derived from the non-destructive sheet strength measuring system equals the sheet strength values determined from the previously input chart of puncture force/sheet strength values.

It will, of course, be understood that numerous modifications of the present invention, in its various aspects, will be apparent to those skilled in the art, some being apparent only after study and others being merely matters of routine machine design. For example, rather than incorporating the cross direction and machine direction puncture blades into the split ring non-destructive sensor of U.S. Pat. No. 4,866,984, as illustrated in FIG. 2, a separate blade-studded wheel and backing ring could be used. Also, separate wheels, one having one or more machine direction blades and another having one or more cross direction blades can be used in addition to a separate non-destructive sheet strength sensor. Other force measuring devices such as load cells may be used in place of piezoelectric force sensors. As such, the scope of the present invention should not be limited by the particular embodiments described herein but should be defined instead by the appended claims and equivalents thereof.

We claim:

1. A method for determining the strength of a moving sheet of material, comprising the steps of:
   puncturing a moving sheet to create at least one puncture hole in the sheet wherein the sheet is moving in the plane of the sheet;
   sensing the magnitude of the force required to puncture the sheet;
   non-destructively deflecting a portion of the moving sheet with a deflecting force, said deflected portion being spaced from the at least one puncture hole;
   sensing the magnitude of the deflecting force; and
   computing the burst strength of the deflected sheet portion using both the magnitude of the sensed deflecting force and a value indicative of the sensed puncture force.

2. The method of claim 1, wherein at least one puncture hole is elongated in the direction of sheet motion and the computed sheet strength is the cross directional strength of the sheet.

3. The method of claim 2, wherein the sheet material is paper.

4. The method of claim 1, wherein at least one puncture hole is elongated perpendicular to the direction of sheet motion and the computed sheet strength is the machine direction strength of the sheet.

5. The method of claim 4, wherein the sheet material is paper.

6. The method of claim 1, wherein a plurality of puncture holes are created, certain of said holes being elongated in the machine direction and certain other of said holes being elongated in the cross direction, and the computed sheet strength is the Mullen strength of the sheet.

7. The method of claim 6, wherein the sheet material is paper.

8. The method of claim 1, wherein the value indicative of the sensed puncture force is an average of the forces required to create a plurality of puncture holes.

9. The method of claim 8, wherein the sheet material is paper.

10. The method of claim 1, wherein the burst strength of the sheet is computed utilizing an equation having a variable deflecting force value and a constant, wherein the value of the constant is determined based upon the sensed puncture force.

11. The method of claim 10, wherein the sheet material is paper.

12. The method of claim 1, wherein the sheet material is paper.

13. A method for determining the strength of a moving sheet material, comprising the steps of:
   assembling a chart including a plurality of puncture force values wherein each puncture force value is associated in the chart with a particular sheet strength value;
   puncturing a sheet portion to create at least one puncture hole in the sheet, wherein the sheet is punctured while said sheet is moving substantially in the plane of the sheet;
   sensing the force required to puncture the sheet portion; and
   using the chart to determine a sheet strength value based upon the sensed puncture force.

14. A method for determining the strength of a sheet material, comprising the steps of:
   assembling a chart including a plurality of puncture force values wherein each puncture force value is associated in the chart with a particular sheet strength value;
   puncturing a first sheet portion to create at least one puncture hole in the sheet;
   sensing the force required to puncture the first sheet portion;
   using the chart to determine a first sheet strength value based upon the sensed puncture force;
   non-destructively deflecting a second sheet portion with a first deflecting force, said second sheet portion being spaced from the first portion;
   computing a second sheet strength value using the first deflecting force and a sheet strength equation including at least one constant; and
   altering the value of at least one constant of the sheet strength equation to obtain a corrected third sheet strength value which conforms with the first sheet strength value determined from the chart.

15. The method of claim 14, wherein the sheet material is paper.

16. The method of claim 14, further comprising the steps of:
   non-destructively deflecting a third portion of the sheet with a second deflecting force, said third sheet portion being spaced from the first and the second sheet portions;
   computing a fourth sheet strength value using the second deflecting force and said sheet strength equation including the at least one altered constant value.

17. The method of claim 16, wherein the sheet material is paper.

18. A sheet strength measuring system, comprising:
   sheet supply means for moving a sheet through a sheet strength measuring area;
   puncturing means for puncturing a hole through a portion of the sheet while the sheet portion is passing through the strength measuring area; and
   puncture force sensing means for sensing the force exerted by the puncturing means when it punctures the passing portion of the sheet and for generating an output signal indicative of the force.

19. The sheet strength measuring system of claim 18, wherein the puncturing means includes a rotatable wheel having a radially protruding blade.

20. The sheet strength measuring system of claim 19, wherein the blade is elongated and oriented lengthwise in the direction of sheet motion.

21. The sheet strength measuring system of claim 19, wherein the blade is elongated and oriented lengthwise in the direction perpendicular to the direction of sheet motion.

22. The sheet strength measuring system of claim 18, wherein the system further includes a non-destructive sheet strength sensor and means for calibrating the non-destructive sheet strength sensor based upon the output signal of the puncture force sensing means.

23. The sheet strength measuring system of claim 22, wherein the sheet material includes paper.

24. The sheet strength measuring system of claim 18, further including an annular support supporting an annular region of the moving sheet and defining the strength measuring area within the annular support, and wherein the puncturing means includes a rotatable wheel having first and second radially protruding blades, the first blade being elongated and aligned at a first predetermined angle and the second blade being elongated and aligned at a second predetermined angle perpendicular to the first angle.

25. A device for determining sheet strength, comprising:
   a rotatable wheel;
   a blade protruding from the periphery of the wheel;
   force sensing means for generating a signal indicative of the force exerted by said blade when the blade contacts a sheet; and
   means for determining sheet strength based upon said signal.

26. The device of claim 25, wherein said blade is fully retractable into the wheel.

27. The device of claim 25, wherein saiddevice includes a plurality of protruding blades and force sensing means associated with said blades, and wherein certain of said blades are elongated and aligned in a direction parallel to the axis of rotation of the wheel and certain other of said plural blades are elongated and aligned in a direction perpendicular to said axis of rotation.

28. The device of claim 25, further comprising a member of known hardness disposed adjacent the periphery of the wheel for contact with the blade at a known force upon each rotation of the wheel.

29. A method for determining the strength of a moving sheet of material, comprising the steps of:
   puncturing a moving sheet to create at least one puncture hole in the sheet wherein the sheet is moving in the plane of the sheet;
   sensing the magnitude of the force required to puncture the sheet;
   non-destructively deflecting a portion of the moving sheet with a deflecting force, said deflected portion being spaced from the at least one puncture hole;
   sensing the amount of sheet deflection; and
   computing the burst strength of the deflected sheet portion using both a value indicative of the sensed amount of sheet deflection and a value indicative of the sensed magnitude of the puncture force.

30. The method of claim 29, wherein the value indicative of the sensed magnitude of the puncture force is an average of the force required to create a plurality of puncture holes.

31. The method of claim 29, wherein the burst strength of the sheet is computed utilizing an equation having a variable for the amount of sheet deflection and a constant, wherein the value of the constant is determined based upon the sensed puncture force.

32. The method of claim 29, wherein the sheet material is paper.

* * * * *